United States Patent
Kim et al.

(10) Patent No.: US 8,936,940 B2
(45) Date of Patent: Jan. 20, 2015

(54) MASS PRODUCTION OF SECONDARY METABOLITE IN PLANT CELL CULTURE BY TREATMENT OF SACCHARIDE MIXTURE IN MEDIUM

(75) Inventors: Jin-Ah Kim, Jeongeup (KR);
Chang-Heon Kim, Daejeon (KR);
Jai-Young Song, Daejeon (KR);
Ho-Joon Choi, Daejeon (KR)

(73) Assignee: Samyang Biopharmaceuticals Corporation (KR)

( * ) Notice: Subject to any disclaimer, the term of this patent is extended or adjusted under 35 U.S.C. 154(b) by 2053 days.

(21) Appl. No.: 11/915,869

(22) PCT Filed: Jun. 2, 2006

(86) PCT No.: PCT/KR2006/002141
§ 371 (c)(1),
(2), (4) Date: Nov. 29, 2007

(87) PCT Pub. No.: WO2006/129988
PCT Pub. Date: Dec. 7, 2006

(65) Prior Publication Data
US 2009/0317877 A1    Dec. 24, 2009

(30) Foreign Application Priority Data

Jun. 3, 2005  (KR) .......................... 10-2005-0047752
Jun. 2, 2006  (KR) .......................... 10-2006-0049694

(51) Int. Cl.
| | | |
|---|---|---|
| C12N 5/00 | (2006.01) | |
| C12N 5/02 | (2006.01) | |
| C12N 1/38 | (2006.01) | |
| C12P 17/02 | (2006.01) | |

(52) U.S. Cl.
CPC ............... *C12N 5/0025* (2013.01); *C12N 1/38* (2013.01); *C12P 17/02* (2013.01)
USPC .......................................... 435/410; 435/431

(58) Field of Classification Search
None
See application file for complete search history.

(56) References Cited

U.S. PATENT DOCUMENTS

| | | | |
|---|---|---|---|
| 6,069,009 A |   | 5/2000 | Pepin et al. |
| 6,248,572 B1 | * | 6/2001 | Choi et al. .................... 435/123 |
| 6,589,765 B1 | * | 7/2003 | Choi et al. .................... 435/123 |

FOREIGN PATENT DOCUMENTS

| | | |
|---|---|---|
| CA | 2069122 A1 | 11/1993 |
| EP | 1 348 764 A1 | 10/2003 |
| JP | 11-069991 A | 3/1999 |
| WO | WO 93/17121 | 9/1993 |
| WO | WO-93/23555 A1 | 11/1993 |
| WO | WO 96/34110 | 10/1996 |
| WO | WO-97/44476 A1 | 11/1997 |
| WO | WO 99/00513 | 1/1999 |

OTHER PUBLICATIONS

Ellis et al., Taxol Production in Nodule Cultures of *Taxus*, Journal of Natural Products, 1996, vol. 59, No. 3, pp. 246-250, US.
Kim et al., Effect of Subculture and Elicitation on Instability of Taxol Production in *Taxus* sp. Suspension Cultures. Biotechnol. Prog. 2004, 20, 1666-1673.
European Search Report dated Apr. 20, 2009. EP 06 74 7492.
Wickremesinhe et al., *Taxus* Callus Cultures: Initiation, Growth Optimization, Characterization and Taxol Production. The Pennsylvania State University pp. 181-193, 1993.
Kim et al., Development of High Performance Liquid Chromatography for Paclitaxel Purification from Plant Cell Cultures, Samyang Genex Biotech Research Institute, pp. 204-210, Published on Web Oct. 21, 2004.
Wu et al., Study on Enhanced Production of Taxol from *Taxus chinensis* var. *mairei* in Biphasic-liquid Culture, Acta Botanica Sinica, vol. 41, No. 10, Oct. 1, 1999, pp. 1106-1113.
Hirasuna et al., Taxol Production in Suspension Cultures of *Taxus baccata*, Plant Cell, Tissue and Organ Culture, Kluwer Academic Publishers vol. 44, No. 2, Feb. 1, 1996, pp. 95-102.

* cited by examiner

*Primary Examiner* — Debbie K Ware
(74) *Attorney, Agent, or Firm* — Gifford, Krass, Sprinkle, Anderson & Citkowski, P.C.

(57) ABSTRACT

The present invention relates to a method of producing secondary metabolites with a high yield using plant cell culture, and a medium for the production of secondary metabolites. More specifically, the method of the present invention is characterized in that the plant cell culture is conducted by adding a saccharide mixture to the culture medium as a carbon source, to increase the productivity of the secondary metabolites. For example, the present invention establishes the method of increasing the productivity of secondary metabolites and shortening the culture time by the use of the mixture of glucose and fructose in the plant cell culture, thereby contributing in producing useful secondary metabolites on an industrial scale using plant cell culture.

5 Claims, 7 Drawing Sheets

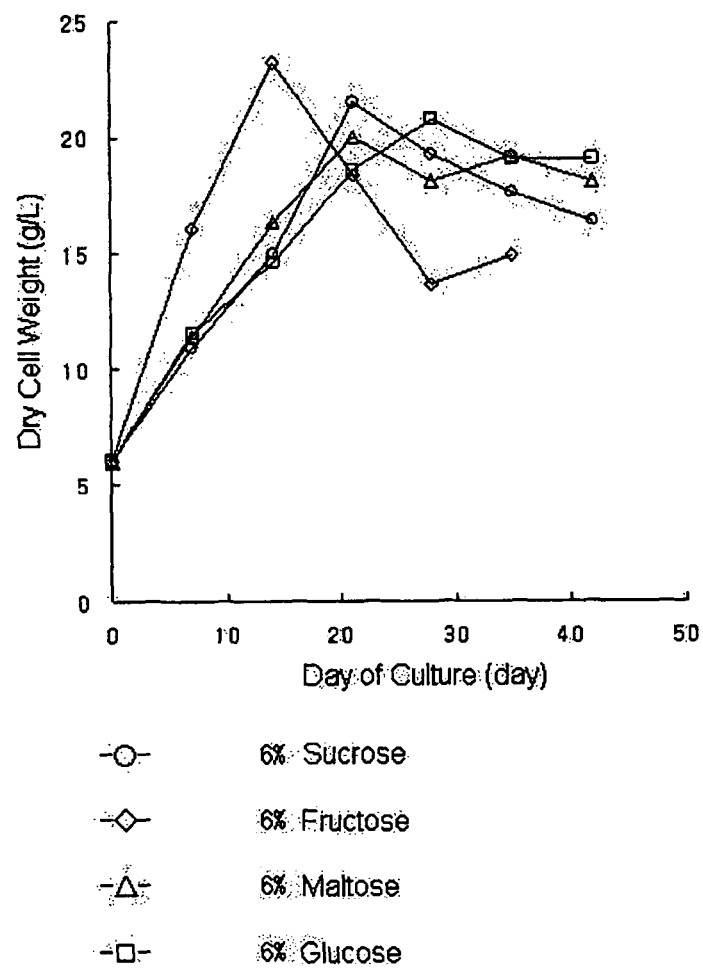

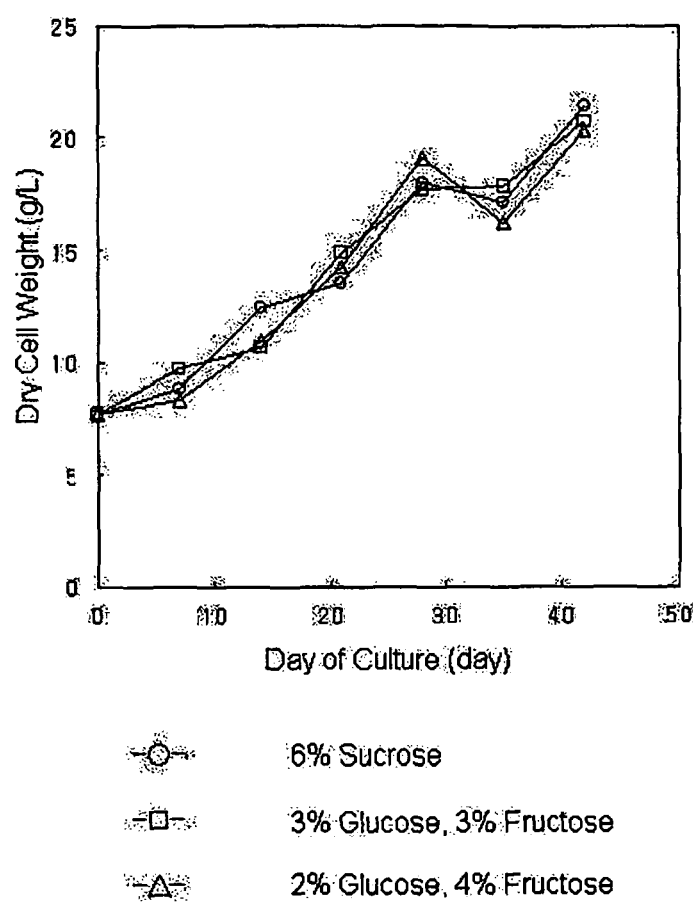

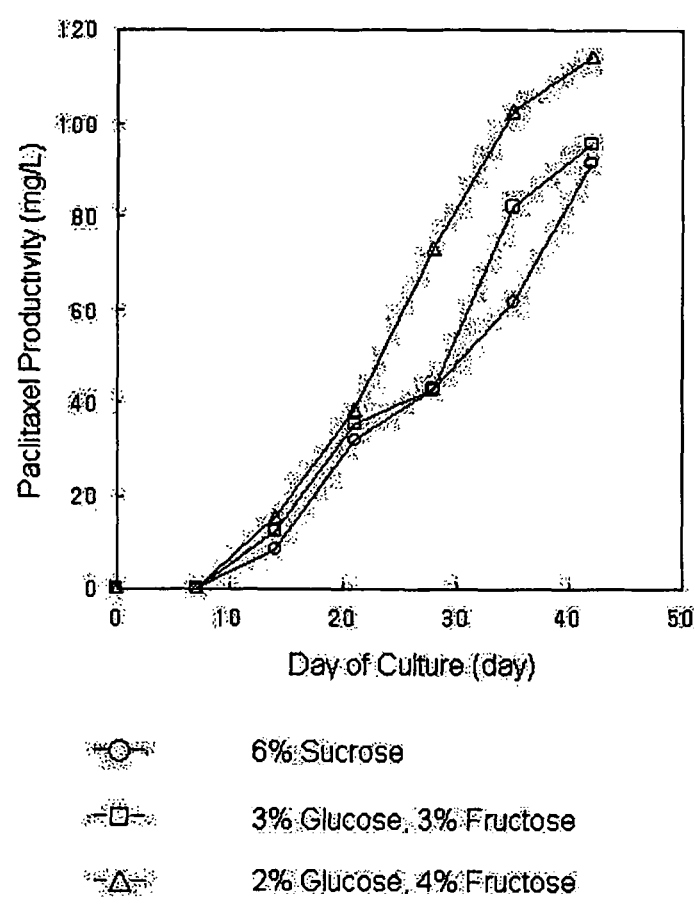

-○- Growth with 3% Sucrose - Production with 6% Sucrose
-□- Growth with 3% Sucrose - Production with 4% Sucrose+2% Fructose
-◇- Growth with 2% Sucrose+1% Fructose - Production with 6% sucrose
-△- Growth with 2% Sucrose+1% Fructose - Production with 4% Sucrose+2% Fructose

US 8,936,940 B2

MASS PRODUCTION OF SECONDARY METABOLITE IN PLANT CELL CULTURE BY TREATMENT OF SACCHARIDE MIXTURE IN MEDIUM

CROSS REFERENCE TO RELATED APPLICATIONS

This application is the U.S. national phase of PCT International Patent Application No. PCT/KR2006/002141 filed Jun. 2, 2006, which claims priority of Korean Patent Application No. 10-2005-0047752 filed Jun. 3, 2005 and Korean Patent Application No. 10-2006-0049694 filed Jun. 2, 2006.

BACKGROUND OF THE INVENTION (a) Field of the Invention

The present invention relates to a method for mass production of secondary metabolite using plant cell culture, and a culture media used therefor. More specifically, the present invention provides a method of producing secondary metabolite using plant cell culture by treating the culture media for plant cell culture with a saccharide mixture of at least two saccharides, to stimulate plant cell growth and increase the productivity of the secondary metabolite.

(b) Description of the Related Art

Plants are useful sources for producing a wide variety of secondary metabolites which are used as pharmaceuticals, pesticides, spices, pigments, food additives, cosmetics and the like. However, while the demands for secondary metabolites in various areas of industry are increasing, the supply of secondary metabolites produced by extraction from plants is limited. Therefore there have been efforts to commercially mass-produce secondary metabolites of plant origin by using plant cell culturing techniques (Stockigt et al., Plant Cell Tissue Org. Cult. 43: 914-920, 1995).

However, mass production of secondary metabolites through plant cell culture is still difficult due to problems such as instability of cultured cell lines, low productivity slow growth, scale-up cultivation and the like.

Various efforts have been made to try and overcome the low productivity in plant cell cultures, and they include the following methods: 1) adjustment of nutrient sources in the media such as addition of sucrose, nitrate salts, phosphate salts, growth regulators, and precursors; 2) optimization of the culture environments such as temperature, lighting, pH of the medium, shaking and aeration conditions; 3) treatment with elicitors to enhance productivity; 4) permeabilization of cell membranes and two-phase culture for effective recovery of secondary metabolites; and 5) metabolic engineering which enhances productivity of secondary metabolites by modifying genes involved in the biosynthesis of secondary metabolites or introduction of exogenous genes.

However, these trials were only effective for particular plant cells or secondary metabolites, and a method that can be generally applied to most plant cell cultures and secondary metabolites has not yet been established.

In general, the plant cell is cultured in an enriched culture media including various nutrients required for cell growth. The productivity of the secondary metabolite can be increased by controlling the nutrients, which are saccharides, nitrates, phosphates, growth regulators, and precursors required for producing the secondary metabolite, etc.

A carbon source is required for supplying the carbohydrate for the plant tissue culture or cell culture. Sucrose and glucose are most commonly used as a carbon source. In addition, fructose, lactose, maltose, galactose, and starch are used. Sorbitol is good for culturing a plant cell derived from a plant belonging to Rosaceae and apple tree, fructose is used for culturing apple rootstock M9 and Dedrobium, and glucose is suitable for wheat anther culture. Sucrose is generally used in a concentration of 2-3%, and can be used at a concentration of 5-12% in some cases. Glucose is used widely for culturing a plant cell of monocotyledon plant (Plant tissue culture and technique, HyangMunSa, 1987).

The preferred carbon sources vary depending on the species of plant, or the kind of cultured tissues or cells in plant cultures. Especially, in the case of the plant cell culture for production of secondary metabolites, the cell growth and the productivity of the secondary metabolites are affected by the carbon source.

There have been many attempts to produce plant cell-originated secondary metabolites on a large scale using plant cell culture techniques. However, there has been no report on a method for mass production of the secondary metabolites by use of a saccharide mixture as a carbon source for culture, which can be widely and generally applied to most plant cell culture and secondary metabolite production.

SUMMARY OF THE INVENTION

The object of the present invention is to provide a method for increasing the productivity of secondary metabolites in plant cell culture that comprises a step of treating with a saccharide mixture of at least two saccharides Another object of the present invention is to provide a culture medium for growth of plant cells and for production of secondary metabolites, comprising a saccharide mixture of at least two saccharides.

BRIEF DESCRIPTION OF THE DRAWINGS

FIG. 1A shows a change in dry cell weight of *Taxus chinensis* cell line SYG-1 that is cultured by treatment with sucrose, fructose, maltose, or glucose in accordance with Example 1.

FIG. 2A shows a change in dry cell weight of *Taxus chinensis* cell line SYG-1 that is cultured by treatment with the mixture of glucose and fructose in accordance with Example 2, and FIG. 2B shows the production pattern of paclitaxel in *Taxus chinensis* cell line SYG-1 that is cultured by treatment with the mixture of glucose and fructose in accordance with Example 2.

DETAILED DESCRIPTION OF THE PREFERRED EMBODIMENTS

Figure 1B:
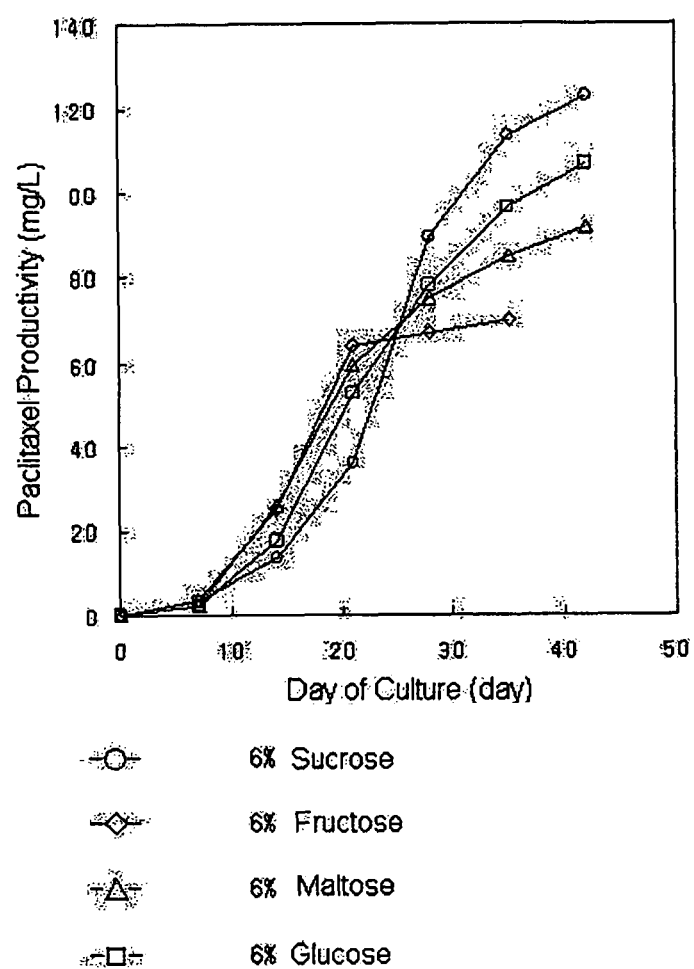
FIG. 1B shows the production pattern of paclitaxel in *Taxus chinensis* cell line SYG-1 that is cultured by treatment with sucrose, fructose, maltose, or glucose in accordance with Example 1.

Exemplary embodiments of the present invention will hereinafter be described in detail with reference to the accompanying drawings.

The present invention provides a method of producing secondary metabolites through plant cell culture, by culturing plant cells in a medium for plant cell culture to which a saccharides mixture of at least two selected from the group consisting of monosaccharides, disaccharides, polysaccharides, and alcohols is added as a carbon source to increase the productivity of secondary metabolites. In addition, the present invention provides a medium for the growth of plant cells or for the production of secondary metabolites in plant cells containing at least two selected from the group consisting of monosaccharides, disaccharides, polysaccharides, and sugar-alcohols, as a carbon source.

Hereinafter, the present invention will be described in detail.

In order to find a method to effectively increase the productivity of secondary metabolites, which can be generally applied to various plant cell cultures, the present inventors conducted a plant cell culture by using a medium containing a mixture of at least two saccharides.

In general, plants produce secondary metabolites growth-independently, and in the case of a cell culture, secondary metabolites are cell growth dependently or independently produced. However, based on the fact that although secondary metabolites are produced regardless of the rate of cell growth, the cell growth may affect the metabolism of plant cells, the present inventors conducted a plant cell culture by adding a mixture of at least two saccharides to a culture medium as a carbon source. As a result, the present inventors have found that the growth of a cell is stimulated and the productivity of secondary metabolites is increased. In addition, the inventors have also found that when a mixture of at least two saccharides are added as a carbon source to a medium for plant cell culture, the period of culture is shortened compared with the case of adding sucrose only as a carbon source.

The present inventors intended to search an optimal combination of at least two saccharides used as a carbon source and a mixture ratio therebetween, that are suitable for the growth and productivity of a cell. To achieve this, in the present invention, the combination of at least two saccharides and the mixture ratio are controlled, as a result, it is increased the production of secondary metabolites.

Therefore, the present invention relates to a method of mass production of secondary metabolites through plant cell culture, by culturing plant cells in a medium for plant cell culture to which a saccharide mixture of at least two saccharides is added as a carbon source, to increase the yield of secondary metabolites.

In the method of mass production of secondary metabolites according to the present invention, the saccharide mixture used as a carbon source may be a mixture of at least two selected from the group consisting of monosaccharides, disaccharides, polysaccharides, and sugar-alcohols. The saccharides, which may be used as a carbon source in the present invention, are shown in Table 1 below, but they are only for illustration, and the saccharides used should not be limited thereto.

TABLE 1

| Monosaccharides | Disaccharides | Polysaccharides | Sugar-Alcohol |
| --- | --- | --- | --- |
| Glucose | Sucrose | Raffinose | Sorbitol |
| Fructose | Melibiose | Amylose | Mannitol |
| Mannose | Trehalose | Starch | Glycerol |
| Ribose | Cellobios | | |
| Arabinose | Lactose | | |

TABLE 1-continued

| Monosaccharides | Disaccharides | Polysaccharides | Sugar-Alcohol |
| --- | --- | --- | --- |
| Xylose | | | |
| Galactose | | | |

In an embodiment of the present invention, the saccharide mixture containing at least two saccharides may be a mixture of glucose and fructose, or a mixture of sucrose and fructose. The mixture ratio (glucose:fructose) by weight of glucose and fructose may be 1:5 to 5:1, and preferably 1:2 to 1:1. If an amount of fructose added to the medium is excessively higher than that of glucose, the cells cultured in the medium has accelerated cell growth. However, due to the excessively accelerated cell growth, cell death (necrosis) occurs disadvantageously before the productivity of secondary metabolites becomes increased.

In another embodiment, when paclitaxel and taxane compounds are produced by culturing a plant cell derived from *Taxus chinensis*, the mixture of glucose and fructose may be used as a carbon source, and the mixture ratio (glucose:fructose) by weight of glucose and fructose may be 1:5 to 5:1, preferably 1:2 to 1:1, and more preferably 1:2.

In still another embodiment, when using the mixture of glucose and fructose, it may be possible that all or part of the glucose be substituted by sucrose which is decomposed into glucose and fructose in a ratio of 1:1 in the culture media. In this case, the amount of sucrose in the mixture of sucrose and fructose may be suitably determined by considering the ratio of glucose and fructose decomposed from sucrose, so that the ratio of glucose and fructose falls to the above range thereof. For example, the mixture ratio (sucrose:fructose) by weight of sucrose and fructose may be 1:4 to 4:1, preferably 1:2 to 2:1, and more preferably 2:1.

According to the inventors' findings, in case sucrose is solely used in media as a carbon source, the productivity of secondary metabolites is stagnated, when fructose begins to be used after consumption of the glucose decomposed from sucrose. In case a monosaccharide such as glucose or fructose is solely used in the media as a carbon source, such stagnation of productivity does not occur at the middle of culture, but the productivity of secondary metabolites is lower than that of the case using sucrose. Therefore, if a mixture of glucose and/or fructose in a suitable mixture ratio is added to the culture media, it may change the transition time of the saccharides used as a carbon source, thereby affecting the productivity of secondary metabolites. The present invention is based on such recognition, that in producing secondary metabolites by plant cell culture, the mass production of secondary metabolites can be achieved by using a saccharide mixture such as mixture of glucose and fructose, or fructose and sucrose, instead of sucrose, as a carbon source, and by controlling the mixture ratio of glucose and fructose, or fructose and sucrose to an optimum ratio.

There are a wide variety of secondary metabolites that can be produced from plants, and the techniques applied to the production of secondary metabolites may vary depending on characteristics of plant species to produce secondary metabolites and the secondary metabolites to be produced therefrom. The method in accordance with the present invention for mass production of secondary metabolites in plant cell culture can be applied to all plant cells that can produce secondary metabolites. The method can be preferably applied to various plant cells exhibiting low productivity of secondary metabolites, in particular, *Taxus* genus cells used for producing paclitaxel which is proven to be effective in treatment of treatmentresistant ovarian cancer and breast cancer, to remarkably increase the productivity of secondary metabolites, thereby the industrial-scale production of paclitaxel can be achieved. Therefore, in a preferable embodiment, the method for mass production of secondary metabolites by a plant cell culture according to the present invention may be applied to cells of various *Taxus* species belonging to the *Taxus* genus, to remarkably increase the productivity of secondary metabolites thereof. The method of the present invention may be applied to the production of any secondary metabolites produced by plant cells, for example, paclitaxel or taxane compounds, but is not limited thereto. The paclitaxel and taxane compounds are produced by a plant cell derived from the *Taxus* sp. plant.

The method of culturing a plant cell and the culture media for plant cell may be applied for any plant cells, and is not limited. For example, the plant cell is derived from a plant selected from the group consisting of *Taxus bacata*, *Taxus brevifolia*, *Taxus canadensis*, *Taxus chinensis*, *Taxus cuspidata*, *Taxus floridana*, *Taxus globosa*, *Taxus media*, *Taxus wallichiana*, and *Taxus yunnanensis*.

In the present invention, any media for plant cell culture which are known in the relevant art may be used, wherein the carbon source contained therein may be substituted with the saccharide mixture as above. As well known in the field of plant cell culture, the culture medium for plant cell culture may contain nutrients, and other factors required for maintaining the cell growth, such as carbon sources, nitrogen sources, salts, vitamins, and the like. The culture media widely used in a plant cell culture may be used in the present invention, wherein various additives may be added thereto, or some components omitted, as occasion demands. The culture media for plant cell culture used in the present invention may be non-limitedly selected from the group consisting of Anderson rhododendron medium, CHU(N6) medium, CLC/Ipomoea medium, Chee & Pool (C2D) vitis medium, De greef & jacobs medium, DKW/JUNGLANS medium, Eriksson(er) medium, Gamborg B5 medium, Gresshof & doy (DBM2) medium, Hellers medium, kao michayluk medium, knudson corchid medium, Lindemann Orchid medium, Litvay medium, Linsmaier & Skoog medium, McCowns woody plant medium, Murashige & Skoog medium, murashige & Miller medium, nitsch medium, NLN medium, orchimax medium, quoirin & Lepoivre medium, rugini olive medium, schenk & hildebrandt medium, S-Medium, vacin and went medium, white medium, westvaco WV3 medium, and a modified medium thereof. Herein, the term 'the conventional media (or medium) for plant cell culture' is intended to include the above listed media.

In an embodiment of the present invention, a modified Gamborg B5 medium including casein hydrolysate (Gamborg et al., Can. J. Biochem., 1968, which is incorporated as a reference herein) may be used in the plant cell culture, and the modified Gamborg B5 medium as shown in Table 2 may be preferable to produce secondary metabolites.

TABLE 2

| Component | Content (mg/L) |
|---|---|
| Inorganic salt | |
| $CaCl_2$ anhydride | 113.23 |
| $CoCl_2 \cdot 6H_2O$ | 0.025 |
| $CuSO_4 \cdot 5H_2O$ | 0.025 |
| $FeSO_4 \cdot 7H_2O$ | 27.8 |
| $H_3BO_3$ | 3.0 |
| KI | 0.75 |

TABLE 2-continued

| Component | Content (mg/L) |
|---|---|
| $KNO_3$ | 2,500 |
| $MgSO_4 \cdot 7H_2O$ | 246 |
| $MnSO_4 \cdot H_2O$ | 10 |
| $NaH_2PO_4 \cdot H_2O$ | 150 |
| $Na_2MoO_4 \cdot 2H_2O$ | 0.25 |
| $(NH_4)_2SO_4$ | 134 |
| $ZnSO_4 \cdot 7H_2O$ | 2 |
| Vitamin | |
| Inositol | 10 |
| Nicotinic acid | 1 |
| Pentosenin acid Ca-salt | 0.874 |
| Pyridoxine•HCl | 1 |
| Riboflavin | 0.015 |
| Thiamine•HCl | 10 |
| Hormone | |
| Naphthalene acetic acid | 10 uM |
| Benzylaminopurine | 0.2 uM |
| Casein hydrolysate | 500 |
| Sucrose | 30,000 |

In an embodiment of the present invention, the medium shown in Table 2 is used as a basic medium, and the medium is used by substituting the carbon source with the saccharide mixture according to the present invention.

In an embodiment of the present invention, the saccharide mixture may be added as substantially the same amount as carbon source contained in the conventional media for plant cell culture. To be consistent with an amount of the known culture medium for plant cells, the amount of saccharide mixture in the culture media may be 2 to 12% (w/v), preferably 4 to 8% (w/v), and more preferably 6% (w/v). Hereinafter, the unit '%' means '% (w/v)', unless it is specifically indicated.

I) In one aspect of the present invention, the plant cell culture may be conducted by using the modified media wherein the carbon source is substituted with the saccharide mixture as above at the initiating stage of the culture.

II) In another aspect of the present invention, the plant cell culture may be conducted by using the modified media wherein the carbon source is substituted with the saccharide mixture as above at the initiating stage of the culture, and then, adding one or more saccharides selected form the group consisting of the saccharides shown in Table 1 as a carbon source at the time when the carbon source originally contained in the media is exhausted, to continue the culture.

III) In another aspect of the present invention, the plant cell culture may be conducted by using the conventional media for plant cell culture, to grow plant cells, and adding at least two saccharides selected form the group consisting of the saccharides shown in Table 1 as a carbon source at the time when the carbon source originally contained in the media is exhausted, to continue the culture.

IV) In another aspect of the present invention, the plant cell culture may be conducted by adding the saccharide mixture as above as a carbon source in the phase of cell growth, the phase of secondary metabolite so production, or both phases. The media used in the two phases may be the same or different from each other, and any one or both of the media may be modified to contain the saccharide mixture.

As described above, in case a carbon source is added in the middle of the culture to enhance the production of secondary metabolites (e.g., II) or III) above), the time to add the additional carbon source is the time when the carbon source contained in the original media is exhausted, and varies depending on the kind of media and plant cell used. Preferably, the additional carbon source may be added to the media when the level of sugar in the media is 2% or less but not completely exhausted. Further, the carbon source may be added to the media so that the sugar concentration in the media reaches to 6% or less, preferably 5% or less, and more preferably 4% or less. For example, the time to add the additional carbon source may be days 7 or later, and preferably, after days 14 or later, after the initiation of culture. In addition, the sugar concentration of the carbon source additionally added may range form 0.1% to 6%, and preferably from 1% to 6%. The additionally added carbon source may be one or more saccharides selected from those illustrated in Table 1.

In the present invention, the carbon source additionally added may be preferably a sole sucrose, a sole fructose, a saccharide mixture of glucose and fructose, or a saccharide mixture of sucrose and fructose. In case the saccharide mixture is used, it may be preferable to make the composition and content thereof as determined above. In case both of the carbon sources used at the initiation of the culture and additionally used in the middle of culture are the saccharide mixtures, the two saccharide mixtures may be the same of different from each other. It is experimentally revealed that when the method of the present invention is applied to the production of paclitaxel, the higher the content of fructose in the saccharide mixture additionally added is, the greater the yield of paclitaxel is obtained. Therefore, it may be preferable to use fructose only, or the mixture of glucose and fructose, or sucrose and fructose, wherein the content of fructose is 50% or more, as the carbon source additionally added in the middle of the culture, in the production of paclitaxel.

Any methods of culturing a plant cell known in the relevant field can be employed in the present invention. For example, the plant cell cultures may include a batch culture, a continuous culture, a fed-batch culture, a semi-continuous batch process, an immobilized culture, a two-phase culture, and the like. The mass production of the secondary metabolite can be achieved by adding a saccharide mixture of at least two saccharides as a carbon source to the plant culture medium during the plant cell culture. The method of culturing a plant cell may be suitably selected depending on the characteristics of the plant cell to be cultured and the secondary metabolites to be produced.

Except for the addition of the saccharide mixture, the condition of the plant cell culture in the present invention may be the same as those in the conventional methods for plant cell culture. In addition, the culture condition specialized for a specific plant cell may be also applied to the present invention. The specific condition that is concretely established in consideration of the characteristics of plant cell to be cultured may also be applied to the present invention.

In an embodiment of the present invention, when the plant cell cultured is derived from genus *Taxus*, the method for mass production of secondary metabolites includes the steps of:

(i) inoculating plant cells derived from genus *Taxus* into a culture media containing the saccharide mixture as a carbon source according to the present invention, and culturing the plant cells at a temperature of 20 to 25° C.; and (ii) continuously culturing the plant cells by changing the culture temperature to range from 26° C. to 32° C.

The method is described in detail in the Korean Patent No. 10-0266448 (incorporated herein entirely as a reference). The time to change the culture temperature may be the time when the cell growth is sufficiently progressed, and the production of secondary metabolites is initiated, which generally corresponds to the proliferative stage or exponential phase in the plant cell growth stages. The time to change the culture temperature may vary depending on various factors, such as the plant cells to be cultured, the secondary metabolites to be produced, the culture temperature, the composition of the medium, and the like. In an embodiment of the present invention, the time to change the culture temperature may be days 10 or later, preferably days 14- to 28, after the initiation of culture. In the plant cell culture according to the present invention, by growing the plant cells sufficiently or to some degree at relatively low temperature, and then, increasing the temperature, as described above, the remarkable increase in the yield of the secondary metabolites such as paclitaxel can be achieved. Such result appears to be caused from the reason that the changed culture temperature may be suitable to newly generate enzymes involved in the biosynthesis of the secondary metabolites including paclitaxel, or close to the optimal temperature of the enzymes involved in the biosynthesis of the secondary metabolites that are already present.

The method for mass production of secondary metabolites may additionally comprise a step of recovering the secondary metabolites produced through a conventional method.

As presented by the present invention, when a saccharide mixture of at least two saccharides is used as a carbon source to produce secondary metabolites, the yield of the secondary metabolites is at least about 30%, preferably at least about 60%, higher than the case that sucrose is solely used. For example, when paclitaxel and taxane compounds are produced by culturing the plant cells derived from *Taxus chinensis*, the yield of paclitaxel is increased two-times.

Further, the present invention also relates to a medium for plant cell culture, that contains a saccharide mixture according to the present invention as a carbon source, and is capable of increasing the productivity of secondary metabolites. The medium for plant cell culture may be a conventional medium for plant cell culture, wherein all or part of the carbon source is substituted with the saccharide mixture according to the present invention. The composition and the contents of each components of the saccharide mixture, the kind of medium for plant cell culture, and the kind of plant cells to be applied to are as the same as described above.

The present invention is further illustrated in the following examples, which should not be taken to limit the scope of the invention.

Example 1

Effect of Single Carbon Source on the Productivity of a Secondary Metabolite

In this example, *Taxus chinensis* SYG-1 cell line (KCTC-0232BP), which produces paclitaxel and taxane compounds, was used for production of secondary metabolites in a plant cell culture.

For proliferation of the cells, a modified Gamborg B5 medium containing 3% sucrose was put into a 250 Ml Erlenmeyer flask. Then, the SYG-1 cells were inoculated into the medium so that the concentration of the cell reached 3 g/L, and cultured under dark conditions at 24° C. and 150 rpm for 14 days.

For production of paclitaxel, a modified Gamborg B5 medium containing 6% sucrose was put into a 250 Ml Erlenmeyer flask, and 50 Ml of the obtained SYG-1 cell culture media was added thereto. The cell culture solution was cultured under dark condition at 24° C. and 150 rpm for 14 days, and further cultured at an elevated temperature of 29° C. for 28 days. In order to increase the productivity of paclitaxel, not only sucrose but also various saccharides as below were used as a carbon source in the plant cell culture.

That is, the SYG-1 cells were cultured in the modified Gamborg B5 medium containing 6% of a saccharide selected from sucrose, glucose, fructose, and maltose, and then, sampled on days 14, 21, 28, 35 and 42 of the culture, to measure the cell growth and paclitaxel productivity The cell growth was evaluated in terms of dry cell weight (DCW). The dry cell weight was determined as a weight of cells measured after filtering a randomly collected plant cell culture through Whatman No. 4 filter paper using a Buchner funnel, and drying the filtered cells in a drying oven at 60° C. for 24 hours.

Paclitaxel productivity was determined by a quantitative analysis method for paclitaxel and taxane compounds widely known to the relevant field of technology (e.g., Korean Patent No. 0266448, which is incorporated hereto entirely as a reference).

The cell growth and the paclitaxel productivity determined from SYG-1 cells cultured in the medium containing a single kind of carbon source are shown in FIGS. 1A and 1B, respectively. As shown in FIGS. 1A and 1B the cells cultured in the media containing sucrose exhibits higher paclitaxel productivity than the cells cultured in the medium containing glucose, fructose, or maltose.

Example 2

Productivity of Paclitaxel by Treating with a Mixture of Glucose and Fructose as a Carbon Source SYG-1 cells were cultured by the same method as in Example 1, except that the medium used contained a mixture of glucose and fructose as a carbon source in the mixture ratio as shown in the following Table 3. On days 14, 21, 28, 35, and 42 of the culture, the cultured cells were sampled, and the cell growth and the paclitaxel productivity of each of the samples were determined according to the method in Example 1.

The obtained results are shown in FIGS. 2A and 2B and Table 3. FIG. 2A shows the changes of dry cell weight depending on the mixture ratio of glucose and fructose. As shown in FIG. 2A, the groups treated with the saccharide mixtures of 2% glucose and 4% fructose, and 3% glucose and 3% fructose, as a carbon source, exhibit an accelerated cell growth equal to that of the group treated with 6% sucrose only, as a carbon source, and at days 35 of the culture, also exhibit the increase of about 67% and about 33% in the productivities of paclitaxel, respectively, compared with the group treated with 6% sucrose only as a carbon source. From the above results, it is shown that the productivity of paclitaxel is increased by treating with a saccharide mixture as a carbon source compared with the case of treating with a single saccharide.

The cells cultured in the medium containing 1% glucose and 5% fructose exhibited a very high level of cell growth, but low paclitaxel productivity. Such result appears to be caused from cell death due to the excessive cell growth.

TABLE 3

| Group | Productivity of Paclitaxel at days 35 of culture (mg/L) |
|---|---|
| 6% sucrose | 61.5 |
| 2% glucose + 4% fructose | 102.4 |
| 3% glucose + 3% fructose | 82.05 |

Example 3

Productivity of Paclitaxel by Treating with a Mixture of Fructose and Sucrose as a Carbon Source SYG-1 cells were cultured by the same method as in Example 1, except that the medium used contained the mixture of glucose and fructose, or sucrose and fructose, in the mixture ratio shown in Table 4, as a carbon source, and sucrose was further added at days 28 and 49 of the culture when the content of sugar in the media was 2% or less, to continue the culture for the extended period of 56 days. On days 14, 21, 28, 35, 49, and 56 after initiation of culture, the cultured cells were randomly sampled, and the cell growth and the paclitaxel productivity of each of the samples were determined according to the method in Example 1.

From the result for the dry cell weight, which is an indicator of the cell growth, it is found that the cells cultured by using the saccharide mixture of glucose and fructose, or sucrose and fructose, as a carbon source, exhibit the cell growth equal to the case using sucrose only.

Figure 3:
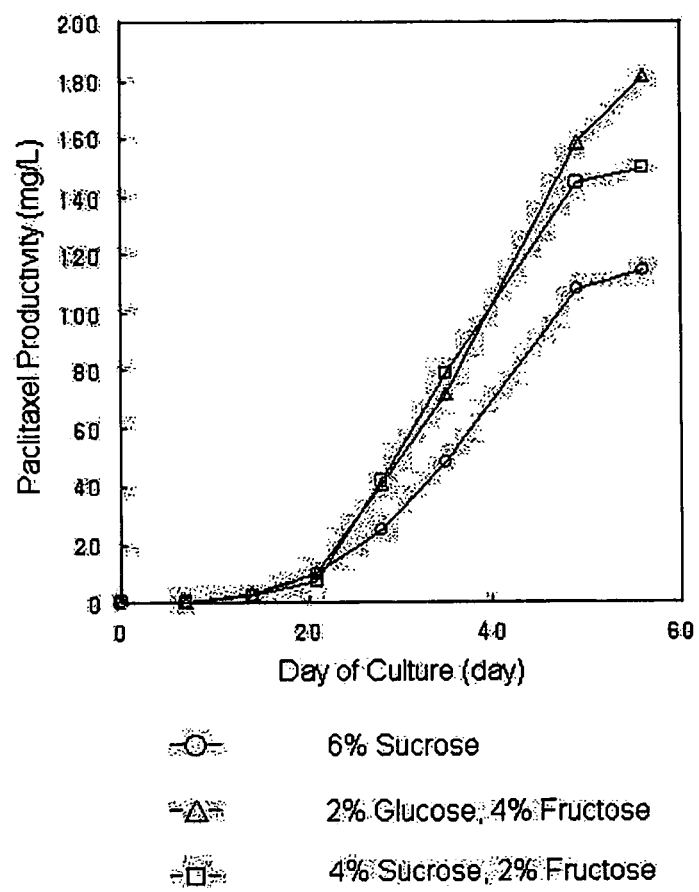
FIG. 3 shows the production pattern of paclitaxel when a single saccharide is further added as a carbon source in the middle of culturing in accordance with Example 3.

The obtained results for the productivity of paclitaxel are shown in FIG. 3 and Table 4. As shown in FIG. 3, the groups treated with the saccharide mixtures of 2% glucose and 4% fructose, and 4% sucrose and 2% fructose, as a carbon source, exhibited an increase of about 58% and about 30% in the productivities of paclitaxel, respectively, compared with the group treated with 6% sucrose only as a carbon source. From the above results, it is shown that the productivity of secondary metabolites is increased by treating with a saccharide mixture as a carbon source compared with the case of treating with a single saccharide.

TABLE 4

| Group | Productivity of paclitaxel at days 56 of culture (mg/L) |
|---|---|
| 6% sucrose | 114.5 |
| 2% glucose + 4% fructose | 181.3 |
| 4% sucrose + 2% fructose | 149.4 |

Example 4

Productivity of Paclitaxel by Adding Additional Carbon Source During the Culture SYG-1 cells were cultured by the same method as in Example 1, except that the medium used contained a mixture of 4% glucose and 2% fructose as a carbon source. At days 21 and 49 after culture when the sugar content in the medium is 2% or less, the additional carbon source as shown in Table 5 was added thereto in the concentration of 2.5%, and then, the culture was continued for the extended period. On days 14, 21, 28, 35 and 49 after initiation of culture, the cultured cells were randomly sampled, and the paclitaxel productivity of each of the samples was measured according to the method in Example 1.

Figure 4:
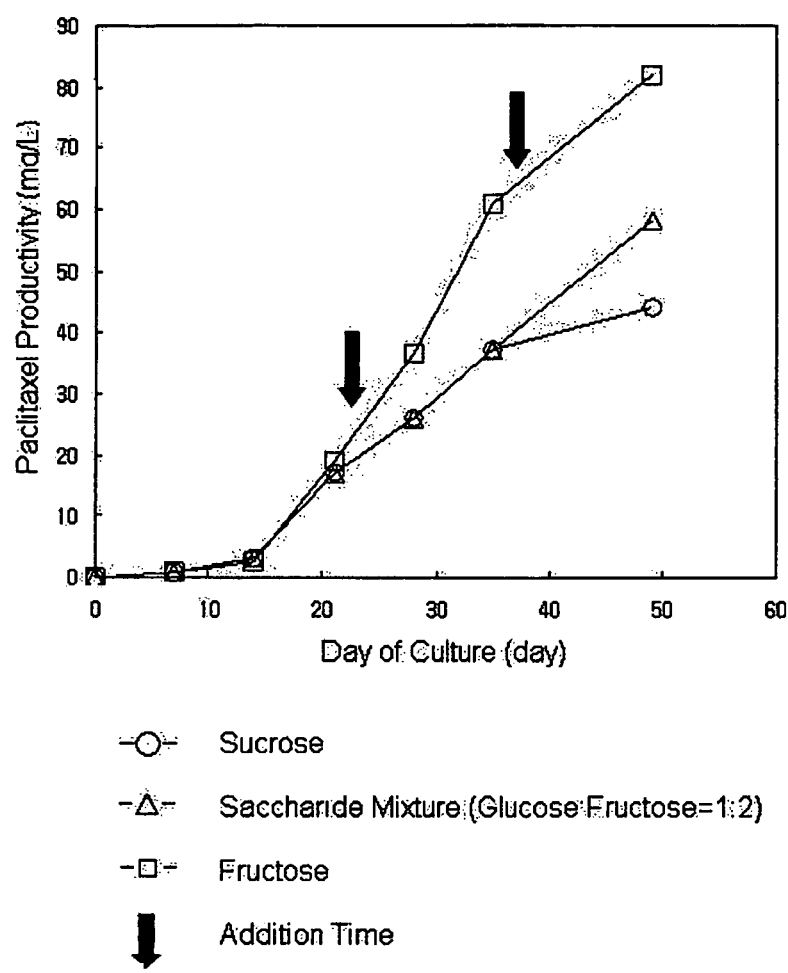
FIG. 4 shows the production pattern of paclitaxel when *Taxus chinensis* cell line SYG-1 is cultured by additional treatment with the mixture of different saccharides as a carbon source in the middle of culturing in accordance with Example 4.

The obtained results for the productivities of paclitaxel when various carbon sources are further added in the middle of the culture wherein a saccharide mixture is added as an initial carbon source are shown in FIG. 4 and Table 5. From the results, it is found that the higher the content of fructose in the additional carbon source, the greater the productivity of paclitaxel.

TABLE 5

| Additional Carbon Source | Productivity of Paclitaxel at days 49 of culture (mg/L) |
|---|---|
| Sucrose | 44 |
| Fructose | 81.9 |
| Glucose:Fructose = 1:2 | 58.4 |

Example 5

Productivity of Paclitaxel by Using Saccharide Mixtures Differently in Cell Growth Phase and Paclitaxel Production Phase For proliferation of the cells, a modified Gamborg B5 medium containing 3% sucrose, or 2% sucrose and 1% fructose was put into a 500 Ml Erlenmeyer flask. Then, SYG-1 cells were inoculated into the medium so that the concentration of the cells reached 3 g/L, and cultured under dark conditions at 24° C. and 150 rpm for 14 days. 50 Ml of the cells cultured for 14 days was put into a modified Gamborg B5 medium containing 6% sucrose, or 4% sucrose and 2% fructose, respectively. The cells were cultured under dark conditions at 24° C. and 150 rpm for 14 days, and further cultured at an elevated temperature of 29° C. for 28 days. On days 14, 21, 28, 35, and 49 after initiation of culture, the cultured cells were sampled, and the paclitaxel productivity of each of the samples was measured according to the method in Example 1.

Figure 5:
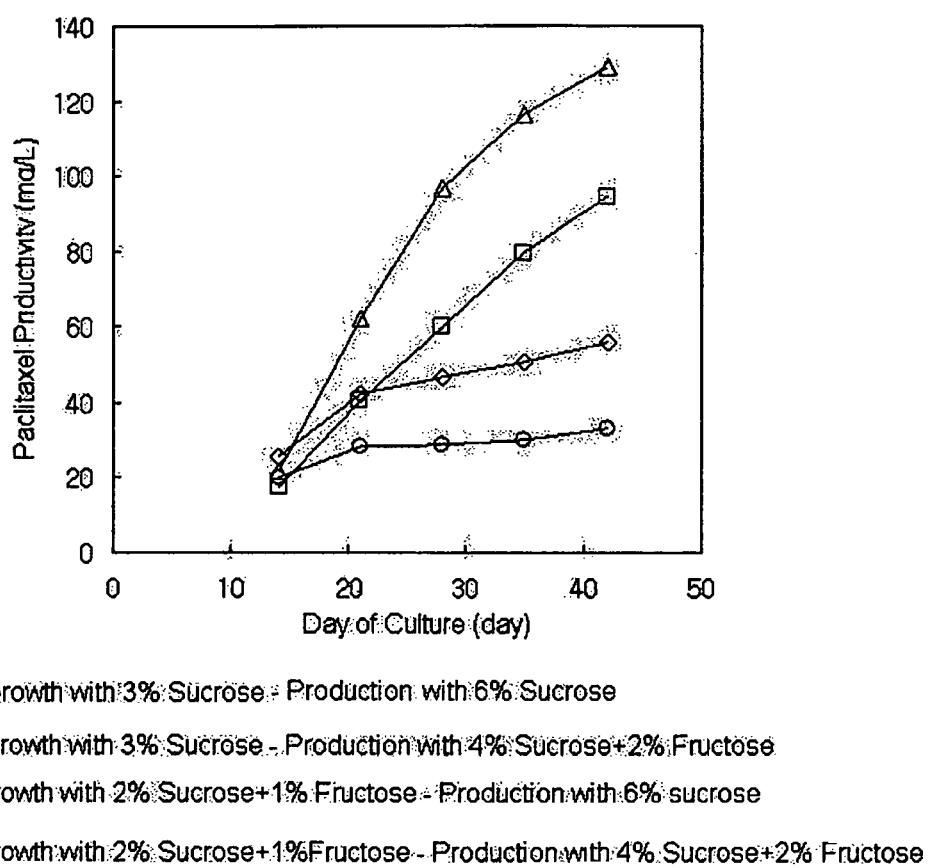
FIG. 5 shows the production pattern of paclitaxel when *Taxus chinensis* cell line SYG-1 is cultured by treatment with saccharide mixtures as a carbon source at plant cell growth stage and secondary metabolite production stage where the saccharide mixtures added at the two stages are different from each other in accordance with Example 5.

The productivity result of paclitaxel obtained by treating the saccharide mixture at both of the cell growth phase and the paclitaxel production phase is shown in FIG. 5 and Table 6.

As shown in FIG. 5 and Table 6, it is found that the case that the saccharide mixture of the present invention is added at the cell growth phase, the paclitaxel production phase, or both phases exhibits a remarkably increased productivity of paclitaxel (by 183%, 67% and 286%, respectively), compared with the case that a single sugar of sucrose is added at both the phases. In addition, when the saccharide mixture is added at both of the two phases, the greatest productivity of paclitaxel is exhibited.

TABLE 6

| The Carbon Source added at Cell Growth Phase | The Carbon Source added at Paclitaxel Production Phase | Productivity of Paclitaxel at day 42 of culture (mg/L) |
|---|---|---|
| 3% sucrose | 6% Sucrose | 33.4 |
| | 4% Sucrose + 2% Fructose | 94.5 |
| 2% sucrose + 1% fructose | 6% Sucrose | 55.9 |
| | 4% Sucrose + 2% Fructose | 129 |

As described above, the method according to the present invention can considerably increase the productivity of secondary metabolites in the plant cell culture which has been known as being very low, and shorten the culturing time, by using the saccharides mixture in the media. Therefore, the method of the present invention is very useful in producing industrially useful plant cell-originated secondary metabolites, such as paclitaxel and the like, on an industrial scale.

What is claimed is:

1. A method of producing secondary metabolites using *Taxus* genus plant cell culture, by culturing the plant cells in a culture medium for plant cell culture to which a saccharide mixture is added as the sole carbon source, to increase the productivity of secondary metabolites,
   wherein the secondary metabolite is paclitaxel,
   wherein the cell culture is conducted by adding the saccharide mixture at a cell growth phase and the secondary metabolite production phase,
   wherein the contents of the saccharide mixture is 2 to 12% (w/v), and
   wherein the saccharide mixture contains glucose and fructose in the mixture ratio by weight of 1:5 to 5:1 or sucrose and fructose in the mixture ratio by weight of 1:4 to 4:1.

2. The method according to claim 1, wherein
   the culture medium is selected from the group consisting of:
   Anderson rhododendron medium, CHU(N6) medium, CLC/Ipomoea medium, Chee & Pool (C2D) vitis medium, De greef & jacobs medium, DKW/JUNGLANS medium, Eriksson(er) medium), Gamborg B5 medium, Gresshof & doy (DBM2) medium, Hellers medium, kao michayluk medium, knudson corchid medium, Lindemann Orchid medium, Litvay medium, Linsmaier & Skoog medium, McCowns woody plant medium, Murashige & Skoog medium, murashige & Miller medium, nitsch medium, NLN medium, orchimax medium, quoirin & Lepoivre medium, rugini olive medium, schenk & hildebrandt medium, S-Medium, vacin and went medium, white medium, westvaco WV3 medium, and a modified medium thereof;
   the original carbon source is excluded therefrom; and
   the saccharide mixture contains glucose and fructose in the mixture ratio by weight of 1:5 to 5:1 or sucrose and fructose in the mixture ratio by weight of 1:4 to 4:1 as a carbon source in the amount of 2 to 12%(w/v) in respect to the media.

3. The method according to claim 1, wherein the plant cell is derived from a plant selected from the group consisting of *Taxus bacata, Taxus brevifolia, Taxus canadensis, Taxus chinensis, Taxus cuspidata, Taxus floridana, Taxus globosa, Taxus media, Taxus wallichiana* and *Taxus yunnanensis*.

4. The method according to claim 1, wherein the plant cell culture is conducted by the method selected from the group consisting of a batch culture, a continuous culture, a fed-batch culture, a semi-continuous batch process, an immobilized culture, a two-phase culture, and a two stage culture.

5. The method according to claim 1, wherein the plant cell culture is conducted by:
   (i) culturing plant cells into the medium for plant cell culture containing the saccharide mixture at the temperature of 20 to 25° C.; and
   (ii) continuously culturing the plant cells by changing the culture temperature into the range from 26° C. to 32° C.

* * * * *